(12) United States Patent
MacHill

(10) Patent No.: US 9,005,186 B2
(45) Date of Patent: Apr. 14, 2015

(54) OPERATING ELEMENT FOR MEDICAL, PREFERABLY SURGICAL INSTRUMENTS WITH THREE-FINGER HOLD

(71) Applicant: Aesculap AG, Tuttlingen (DE)

(72) Inventor: Martin MacHill, Rietheim-Weilheim (DE)

(73) Assignee: Aesculap AG, Tuttlingen (DE)

( * ) Notice: Subject to any disclaimer, the term of this patent is extended or adjusted under 35 U.S.C. 154(b) by 51 days.

(21) Appl. No.: 13/714,629

(22) Filed: Dec. 14, 2012

(65) Prior Publication Data

US 2013/0165909 A1 Jun. 27, 2013

(30) Foreign Application Priority Data

Dec. 15, 2011 (DE) .......................... 10 2011 056 503

(51) Int. Cl.
 *A61B 17/00* (2006.01)
 *A61B 17/16* (2006.01)
 *A61B 17/29* (2006.01)

(52) U.S. Cl.
 CPC .............. *A61B 17/00* (2013.01); *A61B 17/1626* (2013.01); *A61B 17/2909* (2013.01); *A61B 2017/00398* (2013.01); *A61B 2017/00424* (2013.01); *A61B 2017/0046* (2013.01); *A61B 2017/2923* (2013.01); *A61B 17/1628* (2013.01)

(58) Field of Classification Search
 CPC ............... A61B 19/22; A61B 19/2203; A61B 2019/2242
 USPC ............................................................ 606/1
 See application file for complete search history.

(56) References Cited

U.S. PATENT DOCUMENTS

| 1,135,126 | A | | 4/1966 | Hermann |
| 4,246,902 | A | * | 1/1981 | Martinez ......................... 604/22 |
| 2009/0240272 | A1 | | 9/2009 | Shadeck |
| 2010/0168723 | A1 | | 7/2010 | Suarez |

FOREIGN PATENT DOCUMENTS

| DE | 1135126 B | 8/1962 |
| DE | 10262088 B4 | 4/2007 |

(Continued)

OTHER PUBLICATIONS

Aesculap, "Aesculap Power Systems Microspeed® uni—The electric motor system of the future", 2009, pp. 1-16, U.S.A.
Aesculap, "Aesculap Power Systems—Catalogue 2008", 2008, Brochure No. 022711, pp. 1-60.

(Continued)

*Primary Examiner* — Lynsey Crandall
*Assistant Examiner* — Sebastian X Lukjan
(74) *Attorney, Agent, or Firm* — RatnerPrestia

(57) ABSTRACT

An instrument includes a motor unit with a slide or piston. The operating direction of the slide or piston may be adapted to the bending and stretching movement of the user's index finger. A resiliently elastic extension or tongue transfers the bending and stretching movement of the index finger to the slide or piston on the side of the motor unit. The tongue is fixedly coupled to the slide or piston and extends above the handpiece along a gripping portion. The resilient flexibility of the tongue is selected so that it can be easily bent by the index finger resting on the tongue toward the gripping portion of the handpiece, which then serves as a contact or stop element for an operating element at the tongue and thus ensures fixed clamping of the handpiece between the thumb, the middle finger and the index finger.

13 Claims, 3 Drawing Sheets

(56) References Cited

FOREIGN PATENT DOCUMENTS

| | | |
|---|---|---|
| EP | 1629782 A1 | 3/2006 |
| JP | 60083610 U | 6/1985 |

OTHER PUBLICATIONS

German Search Report for Application No. 10 2011 056 503.5 dated Oct. 2, 2012.

* cited by examiner

OPERATING ELEMENT FOR MEDICAL, PREFERABLY SURGICAL INSTRUMENTS WITH THREE-FINGER HOLD

CROSS REFERENCE TO RELATED APPLICATIONS

This application claims the benefit of priority of German Application No. DE 10 2011 056 503.5, filed Dec. 15, 2011, the content of which is incorporated by reference herein for all purposes.

FIELD

The present invention relates generally to motor-driven medical instrumentation, and more specifically to a motor-driven medical instrument that includes a handpiece, drivable tool and motor unit.

BACKGROUND

Motor-driven medical instruments that include electrically-, hydraulically-, or pneumatically-driven motor systems are increasingly employed in various medical fields, such as orthopedics, arthroscopy, neurosurgery and spinal surgery. All of these indications have in common that at the instrument tip of the respective instrument a tool such as a drill, milling cutter or the like is received which is driven by a motor system connected thereto or integral therewith. In order to drive the respective tool in accordance with the current conditions, the respective motor system must be adapted to be optimally controlled by a user.

In particular, in the case of surgical instruments, it is necessary to adapt or vary the operating mode of the tool, i.e. for instance a speed and/or a torque to be maximally applied in accordance with the current state of an operative procedure under precise and stable control.

DE 10 262 088 B4 shows a surgical motor system which is composed of a control device and a foot control associated therewith. A motor connecting cable is connected via a respective coupling member at its one end to the control device and at its other end to a drive or a motor unit by which a tool is adapted to be driven. Via a hand piece coupling different handpieces are mechanically coupled to the motor unit according to requirements. The motor unit then transmits an output signal (drive power) by which the tool provided at a distal end of the hand piece is operated to the control device in response to a request made to the foot control by the user.

It has turned out, however, that a partly required fine control of the motor control system by means of the foot control is not possible already for ergonomic reasons. Furthermore it is fatiguing to the foot when the latter has to remain in a particular position not resting on a plain support over a quite long period of time.

To permit a more sensitive and thus more convenient operation of a motor control system of this type, a manual control has been suggested as a control device by the afore-mentioned document, as well as by the product catalogue of the present applicant, Aesculap "Aesculap Power Systems 2008". The manual control comprises an operating element arranged at the end piece of a motor connecting cable for setting a control signal for operating a motor unit connected to the motor connecting cable which is communicated via the motor connecting cable to a control device and can be operated by the operator when guiding a handpiece coupled to the motor unit. The operating element in the form of an operating lever extends in longitudinal direction along the motor unit in the direction of the distal instrument tip and in the handle area of the hand piece projects radially outwardly therefrom. The operating lever is pivoted with respect to the handpiece and the gripping surface formed at the same for adjusting the motor output power. Accordingly, the operator controls the motor unit by gripping the handpiece and putting a finger, preferably the index finger, onto the lever and pressing the same down in the direction of the gripping piece according to the desired operating mode opposed to a resetting force triggered by a biasing spring.

As the index finger rests on the lever and is utilized for setting the desired operating point of the motor unit, this embodiment has the drawback that in all intermediate positions of the operating lever the handpiece is not held by three but now by merely two fingers while the third one, viz. the index finger, must be held substantially freely above the gripping piece for actuating the operating element. Thus the handpiece rests in the hand in an unstable manner.

Moreover, the handpiece cannot be guided precisely by being clamped between two fingers only, as it is usually known from guiding a pencil during a writing operation. Especially when the pressure onto the tool is increased, which usually would have to be realized almost exclusively by the index finger, the drawback occurs that the fingers laterally gripping the handpiece, viz. the thumb and the middle finger, have to apply the entire force, i.e. the tool contact force, which fatigues the operator's hand already after a short period of time. Moreover, in this case there is a risk that the handpiece can slip away between the two gripping fingers (thumb and middle finger).

The neighboring state of the art can also be inferred from the documents DE 11 35 126 A, US 2009/0240272A1, US 2010/0168723A1, EP 1 629 782 B1 and JP 60 083 610.

Furthermore, in the afore-described manual control it has turned out to be a drawback that the finger actuating the operating lever (index finger) cannot permanently rest for each intermediate position but even has to work against the resetting force of the operating lever during the entire use so as to hold the operating lever at a particular position. This results in the fact that the operating finger for the operating lever fatigues, whereby it becomes increasingly difficult for the operating person to maintain a constant operating condition of the motor unit in the long run.

SUMMARY

Applicants have developed a medical motor-driven instrument that permits an operator's hand to adopt an ergonomically convenient position, which is capable of providing a permanently stable guiding of the handpiece and maintaining a constant setting of a predetermined operating condition.

In one aspect, a motor setting means or element is actuated by a shifting or sliding motion of the index finger of a human hand along a handpiece, or holding piece of the medical instrument such that the actuating index finger exerts or can exert a pressing or holding force onto the handpiece in each shifting, i.e. setting position. In this way, a three-finger hold of the handpiece and thus of the instrument is ensured in each setting position. It is advantageous for constructively materializing this basic principle to provide or couple the setting means with an operating element adapted to be moved along the handpiece and transmitting said longitudinal motion to the setting means.

The motor-driven medical instrument for this purpose may include a handpiece with a tool holder into which a tool can optionally be inserted. Usually, the tool holder is supported to be rotational and/or translational in the handpiece. Further, a motor unit is connected or connectable to the handpiece preferably in the form of a motor cartridge or the motor unit is integrated as a fixed part of the handpiece into the same, the motor unit being operatively connected to the tool holder via a gear system (in the most simple case a drive shaft) so as to transmit a rotary motion of an output shaft of the motor unit to the tool holder for operating the same. At least one setting means/motor setting means is connected or connectable to the (integrated) motor unit or motor cartridge for manually setting the driving force/driving moment/driving power of the motor unit or is integrated in the motor unit, which setting means can be manually actuated by an operator. For this purpose, the setting means includes the afore-mentioned actuating or operating element that is aligned with the handpiece such that the latter preferably can be activated by one (index) finger of the operating hand.

The setting means is preferably designed to have a slide or piston movable substantially in parallel to the motor cartridge and, resp., along an output shaft of the motor unit and, resp., along the handpiece as well as acting on the driving force/driving power of the motor unit to which the operating element is coupled preferably mechanically for a sliding motion to be triggered via the finger. That is to say that the slide or piston is movably supported in axial direction with respect to the preferably cylindrical gripping surface of the handpiece (in the direction of the tool). According to another aspect, the mechanical coupling between the operating element and the slide or piston is such that for the sliding motion of the slide or piston the operating element equally performs a sliding motion substantially along the handpiece (in the direction of the tool).

The operating element that is designed as pivoting lever in prior art now is in the form of a slide element which is held to be displaceable along the gripping surface of the handpiece so as to (finely) adjust the motor power. This configuration permits holding the operating element immobile (not farther movable/pivotal) in the direction of the gripping surface and the hand piece, respectively, at least from a particular point so that it can serve as a substantially fixed support for the actuating finger of the operator during the normal operating condition. This means that the operating finger need no longer be held freely in space above the handpiece but at all intermediate positions rests fixedly on the operating element and thus the handpiece can be clamped between at least three fingers of the hand of an operator in a stable manner.

This technical variation thus enables the handpiece to be guided safely and stably during surgical use and at the same time prevents the operating hand from fatiguing too quickly. Moreover, the holding of the handpiece is ergonomic and thus also counteracts a shaking motion of the operating hand.

It is expressly stated in this context that the afore-mentioned slide or piston can also be replaced with a rotatable element, wherein the manually effected translational motion of the operating element coupled thereto has to be converted to the rotation of the rotatable element. The operating element need not necessarily be a physical part of the setting means, but it can also be integrated in the handpiece or the gripping surface thereof and can then be coupled to the slide or rotatable element.

Handpieces of different geometries, such as handpieces of a straight-cylindrical or offset shape, can be used. Since the operating element and the setting means, respectively, are advantageously provided as standard components, preferably at the plug connector of a power supply hose/cable pack or, in the case of a motor cartridge, can as well be provided at the motor cartridge itself, which in such case preferably would be in the form of a universal motor unit, it is necessary to adapt the setting means to different handpiece geometries in as simple a manner as possible. For this reason, according to an advantageous and alternative configuration of the invention, the mechanical coupling may be arranged between the operating element and the slide or piston by a preferably resiliently flexible rod-shaped or tongue-shaped push/pull member exposed above the handpiece, which push/pull member is substantially fixedly connected to the slide or piston at its proximal end (e.g. in one piece, clamped, glued, welded, riveted or screwed etc.) and at its distal free end supports the operating element preferably in the form of an actuating button or a key. This has the advantage that during operation of the medical instrument, while exploiting the resilient flexibility of the mechanical coupling/extension, the operating element can be pressed preferably against the handpiece and the gripping surface formed at the same applying little force from outside, whereby the handpiece can thus be clamped between the thumb and the middle finger as well as the index finger with the operating element (key) being arranged therebetween. Thanks to the resilient flexibility both straight-cylindrical and offset handpieces can be coupled to the plug connector and/or the motor cartridge, the different geometries being compensated by the push/pull element that is of an elastic or resiliently flexible nature.

The push/pull element may be a leaf spring substantially curved toward the gripping surface of the handpiece with a contact or sliding knob pointing to the gripping surface being formed at the distal free end of said leaf spring. Said sliding or contact knob defines a predetermined contact point having predetermined sliding characteristics on the gripping surface of the handpiece as used, whereby the force required for longitudinally displacing the operating element along the gripping surface can be predetermined and thus be constructively minimized.

The motor unit or the preferred motor cartridge used, respectively, may include an electric, pneumatic or hydraulic motor, the handpiece supporting a mechanical gear system and/or a drive shaft operatively connecting the motor to the tool holder in the handpiece. At the plug casing or, especially in the case of the motor cartridge, at the motor casing the slide or piston for adjusting the motor power can be mounted either externally or internally. In other words, the slide can be supported to be freely accessible at the outside of the plug connector or the motor cartridge or the plug connector or the motor cartridge, resp., is configured to include an inner accommodating portion provided for the slide or piston into which the slide or piston is inserted to be inaccessible from outside. The latter improves the ability to clean the plug connector or the motor cartridge.

Depending on the type of motor drive, the slide or piston can influence, for instance, the electric current or the electric voltage by which an electric motor is driven, or the slide or piston actuates a pressure or current control valve to adjust the supply of a hydraulic or pneumatic pressure medium in the event of a hydraulic or pneumatic drive. It is also possible that the slide or piston is connected to a solenoid for actuating an appropriate valve.

BRIEF DESCRIPTION OF THE DRAWINGS

The foregoing summary and the following description may be better understood when reviewed in conjunction with the drafting figures, of which.

DETAILED DESCRIPTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
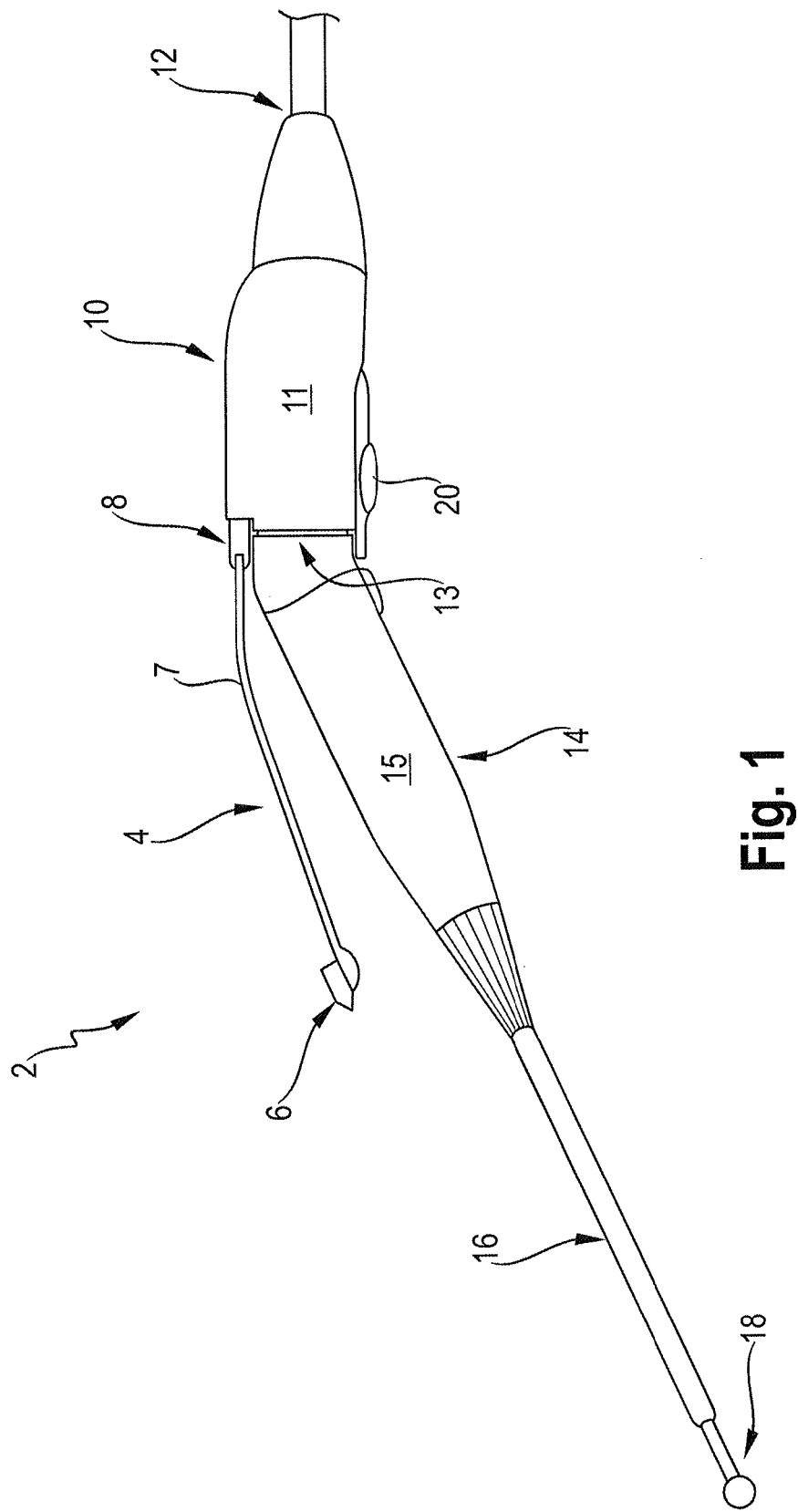
FIG. 1 shows the schematic representation of a motor-driven medical instrument including a setting means as well as an operating element in accordance with a preferred embodiment of the present invention.

In accordance with FIG. 1, a motor-driven medical instrument 2 comprises a handpiece 15, in this preferred embodiment with integrated motor unit, as well as a cable or hose pack or, respectively, power supply line 12 for the power supply to a motor unit which is coupled via a plug connector 11 to the handpiece 15. There is also the possibility to design the motor unit as a motor cartridge which in that case is preferably integrated in the plug connector 11 or the plug casing. It is further imaginable to provide the motor cartridge as an independent component adapted to be coupled to the gripping piece and to which the plug connector 11 can be connected.

In the present example, the plug connector 11 is equipped with a setting means/motor setting means 4, also referred to herein as a setting element, for finely adjusting the motor power to be currently output. The setting means 4 comprises a slide or piston element or, resp., a slide or piston 8 that acts on the setting mechanism of the setting means 4 for adjusting the output motor power and is movable in the direction of or away from the handpiece 15 along (axially with respect to) the plug connector 11. At the slide or piston 8 an operating element/actuating element 6, 7 is fixed or adapted to be fixed which is designed to be positioned radially outside the handpiece 15 for actuation preferably by the index finger 30 of the operating hand 22 of an operator so that the operating element 6, 7 forms a fixed support for the operating finger, preferably the index finger 30, at least in the operating position of the medical instrument 2, i.e. fixedly clamped between at least three fingers of an operating hand.

In detail the handpiece 15 comprises a shank/distal end portion 16 that is arranged at the distal end of the handpiece 1 preferably by attaching or screwing and in which a tool holder (not shown in detail) for any selectable as well as exchangeable tool 18 is housed. The handpiece 15 furthermore includes a sleeve-like grip portion/casing 14 to the distal end of which the shank 16 is connected. At its surface the grip portion 14 forms a (cylindrical) gripping surface which is adapted preferably ergonomically to a three-finger hold of a human hand.

Basically, for handpieces of this species different external shapes such as e.g. a straight-cylindrical or offset cylindrical shape are known, wherein said shapes can equally be provided for the handpiece 15 according to the invention.

Inside the handpiece 15 at least a rotating shaft and a gear system, respectively, is accommodated which operatively connects the tool holder not shown in detail to a coupling member/connection 13 arranged at a proximal, i.e. an axial end of the handpiece 15 opposed to the tool holder. Said coupling 13 consists of an internal electric/pneumatic/hydraulic connecting component (not shown in detail) as well as a plug-socket-type casing portion to which the cable/hose plug connector 11 is mechanically connectable.

As further shown in FIG. 1, the plug connector 11 includes a cartridge-shaped cylindrical casing 10 having a connecting portion corresponding to the coupling member 13 at the distal axial end of the casing 10. Moreover, at the outside of the casing 10 a locking member 20 is provided which is manually operable and in case that the plug connector 11 is coupled to the handpiece 15 is lockable at the handpiece-side coupling 13.

At the proximal axial end of the cartridge-like casing 10 of the plug connector 11 the hose pack 12 is connectable or connected within the handpiece 15 for the power supply of the motor unit. It is noted in this context that the motor unit 11 may include an electric, pneumatic or hydraulic motor and accordingly the hose pack 12 ensures an electric, pneumatic or hydraulic power supply. The coupling 13 and the corresponding connecting portion on the side of the plug connector 11 are configured such that, when the plug connector 11 is connected, the plug casing 10 is fixedly coupled to the handpiece 15, i.e. especially to the gripping portion 14.

As already indicated in the foregoing, the setting means 4 is partly accommodated at/in the plug connector/plug casing 11/10. Concretely speaking, according to FIG. 1 or 2 the plug casing 10 includes a storage shaft or casing portion in which the slide or piston 8 is movably accommodated. As is illustrated in FIG. 1 in this context, the slide or piston 8 protrudes slightly from the plug casing 10 toward the handpiece 15. The sliding direction of the slide or piston 8 consequently is substantially parallel to the longitudinal axis of the cartridge-like plug casing 10 equally toward the handpiece 15 and along the (cylindrical) gripping portion 14 of the handpiece 15. As can further be inferred from FIG. 1, the casing portion for accommodating the slide or piston 8 is provided, with respect to the central axis of the plug casing, on the opposite (diametric) side with respect to the locking member 20.

At the distal axial end of the slide or piston 8 a longitudinal slit is incorporated in the same into which a resiliently flexible extension member in the form of a leaf spring or a resiliently elastic tongue/flexible tongue 7 is pressed, screwed, welded, soldered, glued etc. (The flexible tongue 7 and the slide or piston 8 can also be fabricated in one piece, as a matter of course). This flexible tongue 7 extends in the sliding direction of the slide or piston 8 over and above the entire axial longitudinal portion of the gripping portion 14 up to the connecting point between the shank 16 and the gripping portion 14. The leaf spring 7 is offset/bent slightly in the direction of the surface of the gripping portion 14 at least in the coupling area to the slide or piston 8.

At its free end the leaf spring 7 is configured to have a knob-like projection extending toward the gripping surface 14 of the handpiece 15 and defining a contact as well as slide point with the gripping surface 14 of the handpiece 15. Directly above said knob-like projection an operating element is fixed at the leaf spring 7 in the form of an actuating button or a key 6 forming an engaging or actuating surface which contacts the finger tip of an actuating finger on the side of the actuating hand of an operator.

It is noted in this context that in the case of the embodiment according to FIG. 1 the handpiece 15 used is an offset cylindrical handpiece forming an angle between itself and the cartridge-like plug connector 11 and in which the leaf spring 7, despite its offsetting/bending in the area of the slide or piston 8, has a radial distance from the gripping surface of the gripping portion 14 of the handpiece 15 in the construction position.

The functioning and the handling, resp., of the motor-driven medical instrument 2 according to the invention will be described in detail hereinafter by way of FIG. 2.

Figure 2:
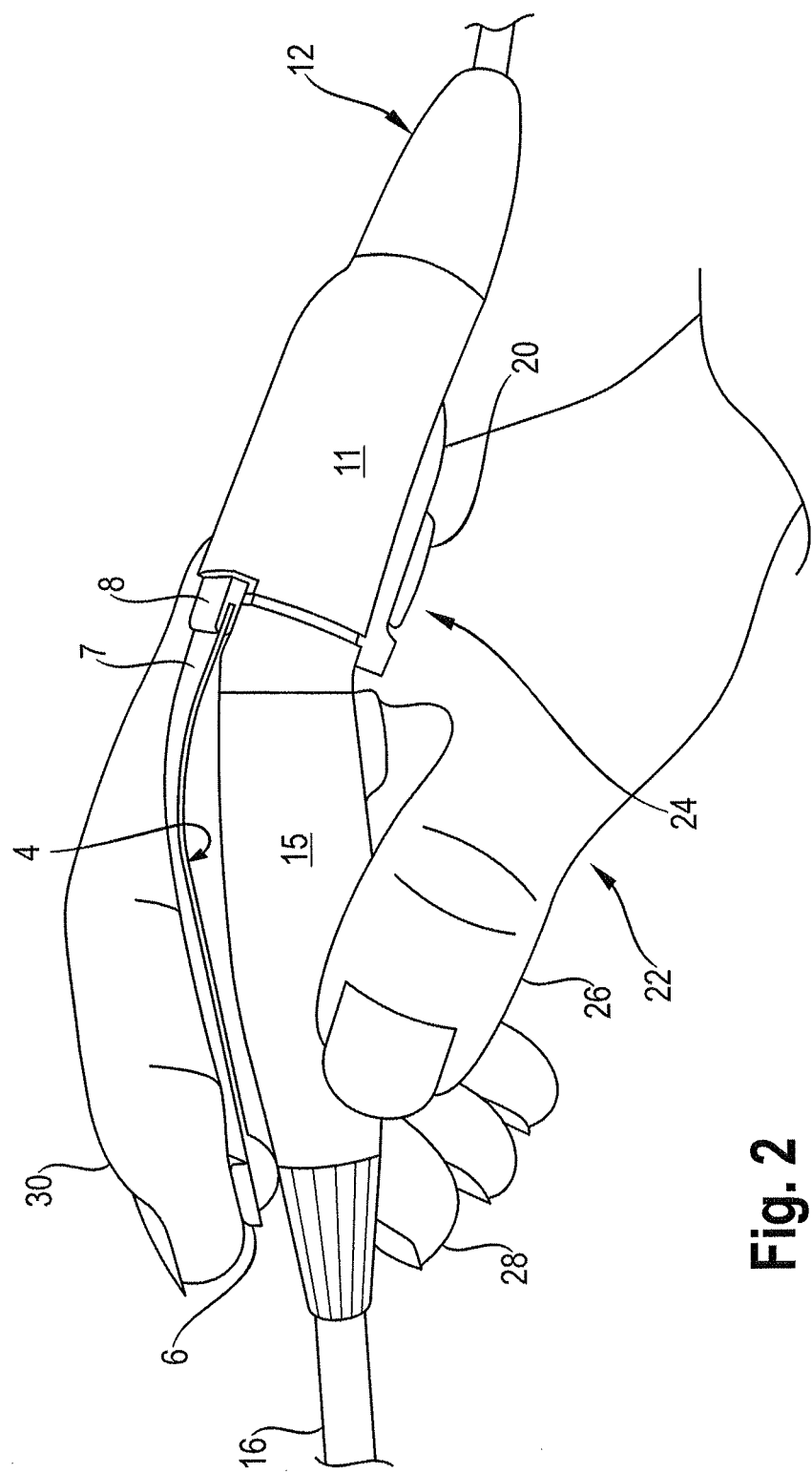
FIG. 2 shows the motor-driven medical instrument according to FIG. 1 in the operating condition, i.e. held by an operator at an ergonomically correct position.

As is illustrated in FIG. 2, the medical instrument 2 according to the invention is held by an operator by the fact that the gripping portion 14 is clamped between the thumb 26 and the middle finger 28 similarly to a pencil and, at the same time, the index finger 30 is laid onto the operating element (key) 6 above the leaf spring 7. The index finger 30 is moved downwards, i.e. in the direction of the gripping portion 14, until the leaf spring 7 rests on the gripping surface with the projection thereof at the free distal end of the leaf spring 7 resulting in a stable holding of the handpiece 15 between the thumb 26, the middle finger 28 and the index finger 30. In this position the leaf spring 7, which is bent to be resiliently elastic in the offset area directly connected to the coupling point to the slide or piston 8, extends substantially in parallel to or along the gripping portion 14 at the outside thereof. Furthermore, in this grip position the plug connector 11 rests on the back of the operator's hand 24 in the area of the locking element 20. So far the medical instrument according to the invention includes four contacting points, viz. the three-finger position as well as the support on the back of the hand 24.

In order to actuate the motor unit which is formed integrally in this case and is not shown in detail, it is only required now to bend or stretch the index finger 30, thereby transforming said bending and stretching movement into a translational motion of the leaf spring 7 along the gripping portion 14 and simultaneously transmitting it to the slide or piston 8 within the plug casing 10. Consequently, the slide 8 performs a sliding motion in response to the bending and stretching movement of the index finger 30 resulting in (finely) adjusting the currently output motor power of the motor unit. During such bending and stretching movement of the index finger 30 the leaf spring 7 slips off its contact knob and the projection on the gripping surface, resp., which thus constitutes a contact surface for the leaf spring and thus also for the index finger 30 in each operating point. The fixed clamping of the medical instrument according to the invention between the three fingers of a human hand 22 is thus ensured in each operating point.

Figure 3:
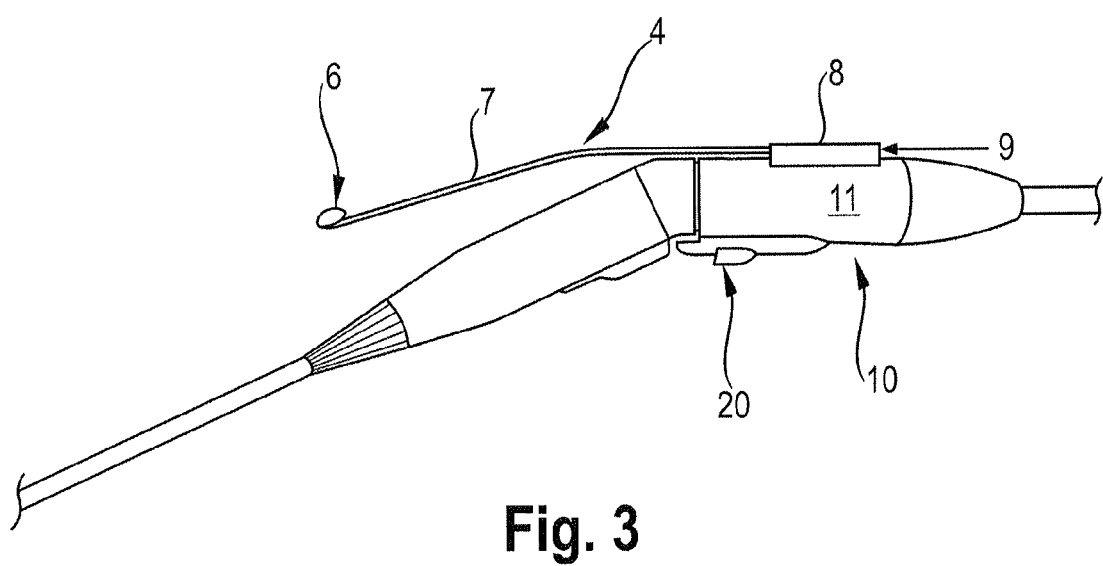
FIG. 3 shows the schematic representation of the motor-driven medical instrument according to the invention in a modification.

FIG. 3 shows a design of the slide or piston 8 at the plug connector 11 modified compared to the embodiment according to FIG. 1.

Accordingly, the plug connector 11 according to FIG. 3 includes no accommodating shaft for accommodating the slide or piston 8 but a sliding surface possibly comprising a longitudinal casing slit not shown in detail on/in which a slide 8 is longitudinally guided. The function of the slide 8 is equal to that of the embodiment of FIG. 1 so that the foregoing description passages can be referred to in this context. Also, the slide 8 according to FIG. 3 includes an actuating element in the form of a resiliently flexible tongue-shaped component (leaf spring) 7 extending along the handpiece 15 especially above the gripping portion 14 and, equally in the construction position, has a curvature toward the gripping surface of the gripping portion 14.

Even in the modification according to FIG. 3, the gripping surface of the gripping portion 14 thus serves as a contact surface for the leaf spring 7 in case that the handpiece 15 is clamped between the thumb, the middle finger and index finger, the latter resting on the actuating button 6 above the leaf spring 7.

While the embodiment according to the invention in accordance with FIG. 1 provides the quasi encapsulated accommodation of the slide or piston 8 and thus achieves the advantage of easier cleaning of the plug connector 11, the modification according to the invention of the medical instrument according to FIG. 3 includes an exposed slide 8 which is movably held merely at the outside of the cartridge-like plug casing 10 and the sliding position of which an operator can thus read especially clearly. Therefore the modification according to FIG. 3 offers the advantage of better visual monitoring of the currently set motor power output.

Finally it is once again referred to the fact that the motor unit need not necessarily be integrated in the handpiece 15, but can also be designed externally as a motor cartridge which then is adapted to be flanged to the handpiece. In this case it is evident to accommodate the external motor unit in the plug casing 10, for instance, wherein the coupling 13 in such case would have to be designed to further include a torque transmission component. It would also be possible, however, to reserve the plug casing 10 shown in the figures exclusively for the motor unit and then to displace the plug connector axially behind said cartridge-like casing.

Summing up, the core of the present invention relates to equipping a cartridge-like motor unit known per se with a slide or piston the actuating direction of which is adapted to the bending and stretching movement of the index finger of an operating hand in the case that a handpiece connected to the motor unit is clamped between the thumb, the index finger and the middle finger like a pencil. In order to transmit said bending and stretching movement of the index finger to the slide or piston on the side of the motor unit, there is provided a resiliently elastic extension or tongue that is fixedly coupled to the slide or piston and extends above the handpiece along the gripping portion formed at the same. The resilient flexibility (elasticity) of the tongue is selected such that the latter can be easily bent by the index finger resting on the tongue toward the gripping portion of the handpiece which in that case serves as a contact or stop element for an operating element disposed at the spring and thus ensures fixed clamping of the handpiece between the thumb, the middle finger and the index finger.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A motor-driven medical instrument comprising:
a handpiece having a gripping surface;
a drivable tool connected to the handpiece; and
a motor unit, the motor unit having a longitudinal axis and operatively connected with a motor setting element, the motor setting element comprising a piston, a flexible extension member fixed to the piston, and an operating element fixed to the flexible extension member,
the piston being axially movable in a direction parallel to the longitudinal axis and operatively connected to the motor unit to adjust a motor power output or a rotational speed of the motor unit in response to a longitudinal position of the piston, the piston axially movable in a direction parallel to the longitudinal axis of the motor unit between a first longitudinal position that sets a first motor power output or a first motor speed, and a second longitudinal position that sets a second motor power output or a second motor speed, the second motor power output or the second motor speed being different than the first motor power output or the first motor speed, respectively,
the flexible extension member being axially movable together with the piston in a direction parallel to the longitudinal axis in response to an actuating force applied to the operating element, and the flexible extension member being bendable toward the gripping surface of the handpiece, in response to the actuating force applied to the operating element.

2. The motor-driven medical instrument according to claim 1, further comprising a rod-shaped or tongue-shaped push/pull element extending along the handpiece so as to couple the operating element at a longitudinal distance from the motor setting element, the push/pull element being resiliently flexible so that it can be manually pressed against the handpiece in the area of the operating element.

3. The motor-driven medical instrument according to claim 1, wherein the handpiece is provided for rotatably or movably accommodating a selectable or particular tool at the distal end portion thereof as well as for transmitting a driving force from the motor unit to the tool, the motor unit being equipped with or operatively connected to the motor setting element for manually setting the driving force, for this purpose the latter including the operating element operable by a finger, wherein the piston is substantially movable along the handpiece and acting on the driving force, to which piston the operating element is mechanically coupled for a sliding motion to be triggered by the finger such that for this purpose the operating element equally performs a sliding motion substantially along the handpiece.

4. The motor-driven medical instrument according to claim 1, wherein the motor unit includes an output shaft extending in the direction of the tool, wherein the piston is aligned along the output shaft.

5. The motor-driven medical instrument according to claim 1, wherein the motor unit is integrated in the handpiece and the motor setting element is provided at or in a plug connector for connecting a power supply line to the handpiece.

6. The motor-driven medical instrument according to claim 1, wherein the motor unit is provided as a motor cartridge formed separately from the handpiece which is connectable or connected to the handpiece at the proximal end thereof.

7. The motor-driven medical instrument according to claim 3, wherein the mechanical coupling is provided by a resiliently flexible, rod-shaped or tongue-shaped push/pull element which at its proximal end is coupled to the piston and at its distal free end holds the operating element in the form of a key or an actuating button.

8. The motor-driven medical instrument according to claim 7, wherein the push/pull element is a leaf spring curved in the direction of a gripping surface of the handpiece at the distal free end of which a contact or sliding knob facing toward the gripping surface is formed or fixed at which the leaf spring is slidably supported against the gripping surface when the operating element is actuated.

9. The motor-driven medical instrument according to claim 8, wherein the handpiece includes a straight-cylindrical or axially bent cylindrical casing the outside of which forms the gripping surface and at the proximal axial end of which a connection for the plug connector or the motor cartridge is disposed.

10. The motor-driven medical instrument according to claim 8, wherein the leaf spring is configured so that it is pressed against the gripping surface by an operating finger upon actuating the operating element irrespective of whether the handpiece has a straight-cylindrical or bent-cylindrical shape.

11. The motor-driven medical instrument according to claim 1, wherein the motor unit is an electric, pneumatic or hydraulic motor, the handpiece comprising a mechanical gear system and/or a drive shaft operatively connecting the motor to a tool holder in the handpiece.

12. The motor-driven medical instrument according to claim 6, wherein the plug connector or the motor cartridge includes a casing which forms an accommodating portion for the piston and/or that the plug connector and/or the motor cartridge includes a casing at the outside of which the piston is slidably guided and/or the piston directly or indirectly controls an electric current, an electric voltage, the pressure or the flow of a hydraulic or pneumatic fluid.

13. The motor-driven medical instrument of claim 1, wherein the flexible extension member comprises a bend in proximity to the piston.

* * * * *